United States Patent
Takayama et al.

(10) Patent No.: US 10,227,562 B2
(45) Date of Patent: *Mar. 12, 2019

(54) PROCESS FOR SORTING MOTILE PARTICLES FROM LESSER-MOTILE PARTICLES AND APPARATUS SUITABLE THEREFOR

(71) Applicant: THE REGENTS OF THE UNIVERSITY OF MICHIGAN, Ann Arbor, MI (US)

(72) Inventors: Shuichi Takayama, Ann Arbor, MI (US); Gary D. Smith, Ann Arbor, MI (US); Timothy G. Schuster, Ann Arbor, MI (US); Brenda S. Cho, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 118 days.

This patent is subject to a terminal disclaimer.

(21) Appl. No.: 15/378,980

(22) Filed: Dec. 14, 2016

(65) Prior Publication Data

US 2017/0137779 A1 May 18, 2017

Related U.S. Application Data

(60) Continuation of application No. 12/061,482, filed on Apr. 2, 2008, now Pat. No. 9,523,075, which is a division of application No. 10/375,373, filed on Feb. 27, 2003, now abandoned.

(60) Provisional application No. 60/359,844, filed on Feb. 27, 2002.

(51) Int. Cl.
| | | |
|---|---|---|
| *C12N 5/071* | (2010.01) | |
| *B01L 3/00* | (2006.01) | |
| *G01N 15/14* | (2006.01) | |

(52) U.S. Cl.
CPC ...... *C12N 5/0612* (2013.01); *B01L 3/502753* (2013.01); *B01L 3/502761* (2013.01); *B01L 3/502776* (2013.01); *G01N 15/1404* (2013.01); *B01L 2200/0636* (2013.01); *B01L 2200/0647* (2013.01); *B01L 2200/0652* (2013.01); *B01L 2300/0864* (2013.01); *B01L 2300/0867* (2013.01); *B01L 2400/0406* (2013.01); *B01L 2400/0457* (2013.01)

(58) Field of Classification Search
None
See application file for complete search history.

(56) References Cited

U.S. PATENT DOCUMENTS

| | | |
|---|---|---|
| 4,574,000 A | 3/1986 | Hunter |
| 4,894,146 A | 1/1990 | Giddings |
| 5,514,537 A | 5/1996 | Chandler |
| 5,932,100 A | 8/1999 | Yager et al. |
| 6,159,739 A | 12/2000 | Weigl et al. |
| 6,193,647 B1 | 2/2001 | Beebe et al. |
| 6,408,878 B2 | 6/2002 | Unger et al. |
| 6,409,832 B2 | 6/2002 | Weigl et al. |
| 6,448,069 B1 | 9/2002 | Cecchi et al. |
| 6,541,213 B1 | 4/2003 | Weigl et al. |
| 6,673,008 B1 | 1/2004 | Thompson et al. |
| 6,695,147 B1 | 2/2004 | Yager et al. |
| 6,695,765 B1 | 2/2004 | Beebe et al. |
| 6,742,661 B1 | 6/2004 | Schulte et al. |
| 6,743,399 B1 | 6/2004 | Weigl et al. |
| 6,807,892 B2 | 10/2004 | Biegelsen et al. |
| 9,523,075 B2* | 12/2016 | Takayama ......... B01L 3/502753 |
| 2002/0068358 A1 | 6/2002 | Campbell et al. |
| 2008/0187991 A1 | 8/2008 | Takayama et al. |

FOREIGN PATENT DOCUMENTS

| | | |
|---|---|---|
| WO | 1998010267 | 3/1998 |
| WO | 2000009648 | 2/2000 |
| WO | 2000056444 | 9/2000 |
| WO | 2001026813 | 4/2001 |
| WO | 2003008102 | 1/2003 |

OTHER PUBLICATIONS

Anderson et al., "Fabrication of topologically complex three-dimensional microfluidic systems in PDMS by rapid prototyping." Anal Chem. Jul. 15, 2000;72(14):3158-64.
Brody et al., "Biotechnology at low Reynolds numbers." Biophys J. Dec. 1996;71(6):3430-41.
Duffy et al., "Rapid Prototyping of Microfluidic Systems in Poly(dimethylsiloxane)." Anal Chem. Dec. 1, 1998;70(23):4974-84.
Mobility definition (retrieved from http://www.thefreedictionary.com/mobility on Jan. 27, 2015, 3 pages).
Smith et al., "Use of postseparation sperm parameters to determine the method of choice for sperm preparation for assisted reproductive technology." Fertil Steril. Mar. 1995;63(3):591-7.
Unger et al., "Monolithic microfabricated valves and pumps by multilayer soft lithography." Science. Apr. 7, 2000;288(5463):113-6.

(Continued)

*Primary Examiner* — Karlheinz R. Skowronek
*Assistant Examiner* — Ronald T Niebauer
(74) *Attorney, Agent, or Firm* — Casimir Jones, S.C.; Tanya Arenson

(57) ABSTRACT

Motile particles are sorted from non-motile particles in a microfluidic sorting device wherein a stream of sort fluid containing motile and non-motile particles is caused to flow adjacent a media stream in non-turbulent fashion through a sort channel, during which flow motile particles cross the interface between the adjacent flow streams, entering the media stream, and forming a motile particle-depleted sort stream. The sorting devices are easily and inexpensively fabricated and have numerous uses, in particular sorting of motile from non-motile sperm.

7 Claims, 3 Drawing Sheets

(56) References Cited

OTHER PUBLICATIONS

Winet et al., "Observations on the response of human spermatozoa to gravity, boundaries and fluid shear." J Reprod Fertil. Mar. 1984;70(2):511-23.
Yale Scientific (Akusobi C 'Does zero gravity exist in space' dated Oct. 2, 2010 retreived from http://www.yalescientific.org/201 0/1 0/mythbusters-does-zero-gravity-exist-in-space) on Jan. 28, 2015, 8 pages).
Weigl et al, "Passive Microfluidics—Ultra-Low-Cost Plastic Disposable Lab-on-a-Chips" Proceedings of Microtag 2000, Enshede, Netherlands, pp. 299-302 (2000).

\* cited by examiner

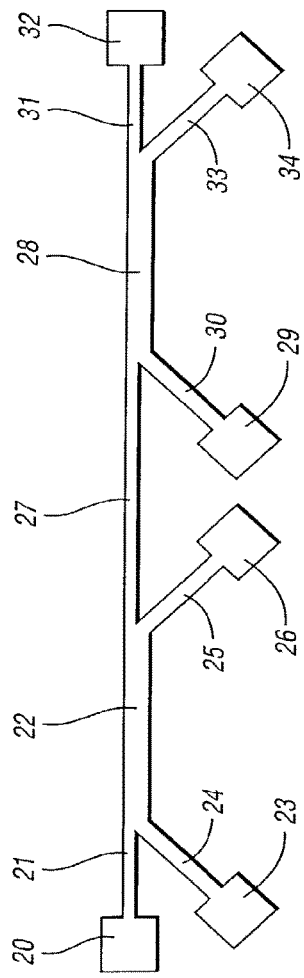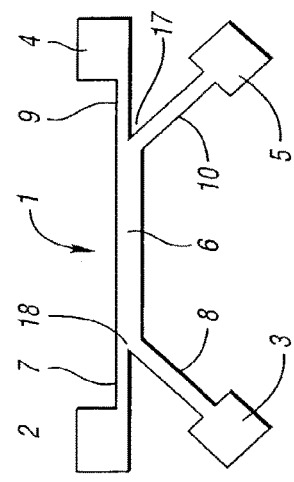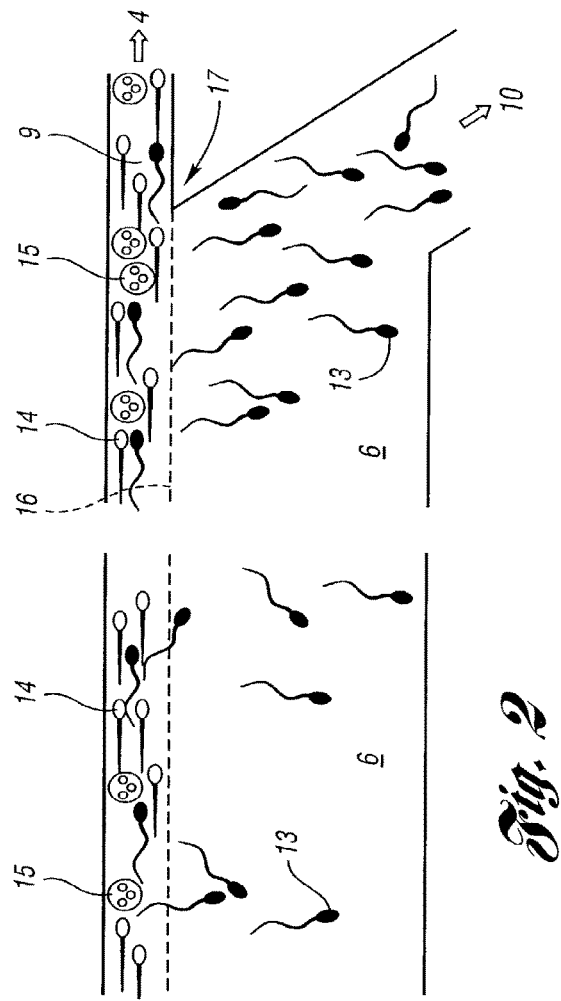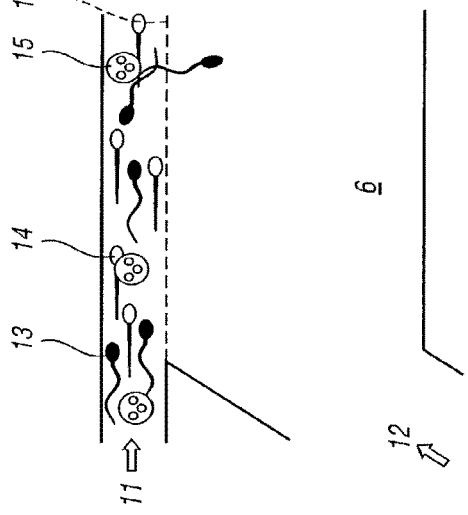

PROCESS FOR SORTING MOTILE PARTICLES FROM LESSER-MOTILE PARTICLES AND APPARATUS SUITABLE THEREFOR

CROSS-REFERENCE TO RELATED APPLICATION

This application is a continuation of U.S. patent application Ser. No. 12/061,482, filed Apr. 2, 2008, which is a divisional of U.S. patent application Ser. No. 10/375,373, filed Feb. 27, 2003, which claims the benefit of U.S. provisional application Ser. No. 60/359,844, filed Feb. 27, 2002 each of which is herein incorporated by reference in their entireties.

This invention was made with government support under HD035125 awarded by the National Institutes of Health. The government has certain rights in the invention.

BACKGROUND OF THE INVENTION

1. Field of the Invention

The present invention pertains to a process for sorting motile from lesser-motile particles, particularly motile and non-motile particles of biological origin, and to apparatus suitable therefor.

2. Background Art

The separation, or "sorting" of motile from lesser-motile and/or non-motile particles has numerous applications, but heretofore has been technologically difficult. For example, in analysis of water supplies, it may be desirable to separate motile bacteria and other microorganisms, including fungi, algae, etc., from those which are non-motile. Identification and enumeration of the various species may thus be facilitated. Examples of motile organisms include flagellated and ciliated bacteria such as *C. elegans*, and other microorganisms, such as paramecia and motile plankton. Either the motile species enriched or motile species-depleted samples, or both, may be independently analyzed, cultured, etc.

An especially significant application is the sorting of sperm cells. For example, in the case of in vitro fertilization, if the donor's sperm count is low, and especially if contaminated with non-motile sperm, deformed sperm of lesser motility than the desired viable sperm, and other cells and seminal debris, the success rate is raised considerably when the motile sperm are used substantially for fertilization attempts. For example, avoidance of aneuploid sperm or DNA fragmented sperm is particularly desirable. In many endeavors, it is desirable to be able to direct the gender of the offspring, for example when the birthing of milk cows is desired. In such cases, it would be advantageous to be able to sort the X- and Y-chromosome containing sperm based on their known motility differences.

Sperm cells from donors with oligozoospermia (low sperm count) have previously been concentrated and to some degree separated from cells and debris having different sizes and/or densities by centrifugation. However, this technique allows incorporation of non-gametes into the enriched sperm sample. These non-gametes, however few there are, release oxygen radicals which are detrimental to continued sperm viability. Moreover, centrifugation is a brute force technique which damages significant numbers of sperm, particularly at the mid-piece and tail regions.

So-called "swim up" techniques are also known, but isolation of the most viable sperm is challenging. S. Smith et al., FERTIL. STERIL. 1995, 63, 591-97. Thus, doctors frequently resort to hand sorting through dead sperm and debris to find sperm which are motile and of distinct morphology, a very time-consuming process.

Applications in biogenetics (biotechnology) also frequently require separation of particles based on their motility. In non-biological application, separation of working microrobots (which are motile) from non-working microrobots is a possible application.

SUMMARY OF THE INVENTION

Sorting of motile and non-motile or lesser-motile particles is accomplished by establishing a non-turbulent and preferably laminar flow stream ("sort stream") containing motile and non-motile or lesser-motile particles to be sorted, and contacting this sort stream with a second non-turbulent and preferably co-laminar media flow stream ("media stream"), providing an exit stream for at least a portion of a motile particle-enriched media flow stream, and an exit stream for a motile particle-depleted sort stream. The mobility of the motile particles allow them to enter the media stream along the interface between the media and sort streams, while non-motile or lesser-motile particles remain substantially within the sort stream. Apparatus suitable for use in the process provide for at least one sort stream inlet, at least one media stream inlet, at least one sort channel, at least one motile particle-depleted sort stream outlet, and at least one motile particle-enriched media stream outlet. The apparatus are preferably relatively small devices prepared by micro-machining or polymer casting techniques, and preferably contain all necessary functionality integrated onto a single "chip."

BRIEF DESCRIPTION OF THE DRAWINGS

FIG. 1 illustrates a simple embodiment of a motile particle sorting device of the present invention;

FIG. 2 depicts sorting of motile from non-motile particles in a sort channel of a device of FIG. 1;

FIG. 3 illustrates one embodiment of series connected sorting devices;

DETAILED DESCRIPTION OF THE PREFERRED EMBODIMENTS

Figure 4:
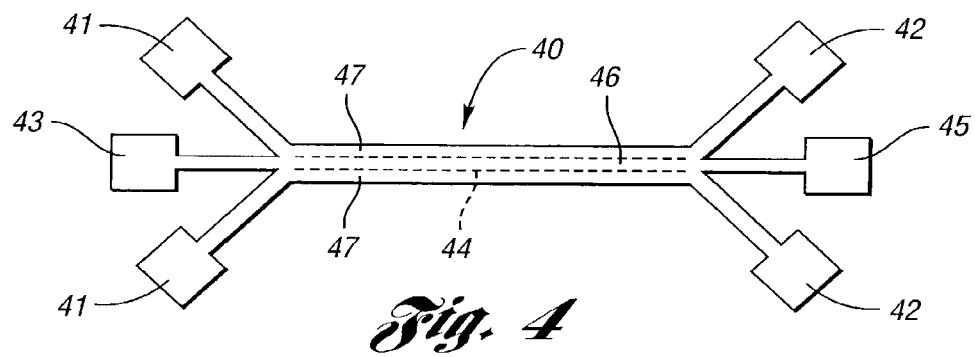
FIG. 4 illustrates a further embodiment of a sorting device with multiple media inlets.

The description of the invention may be facilitated by reference to FIG. 1 which represents one relatively simple embodiment of an apparatus which may be used for practicing the subject invention, and by reference to FIG. 2 which illustrates sorting of motile from non-motile particles. Following these descriptions, additional details of the functioning of the apparatus, its geometry, the nature of fluids and fluid flow, etc., will be explained in greater specificity.

The device of FIG. 1 is shown in schematic form in plan, i.e. as viewed from above. The device 1 embodiment consists of a motile particle sort stream inlet 2 (or motile particle supply reservoir serving as an inlet), a media stream inlet 3 (or media reservoir), a motile particle-depleted sort stream outlet (or reservoir) 4, and a motile particle-enriched stream outlet (or reservoir) 5. Between the inlets 2 and 3 and the outlets 4 and 5 is located a sort channel 6. Connecting the sort channel 6 to the respective inlets and outlets are sort stream inlet channel 7, media stream inlet channel 8, motile particle-depleted sort stream outlet channel 9, and motile particle-enriched media stream outlet channel 10. The width of the sort stream channel must be large enough to allow the particles of interest to pass through effectively without blockage, as is also true of both outlet streams. In general, the inlet streams and outlet streams will have a cross-sectional area less than the sort channel. The relative cross-sections will be dependent on the flow volume and flow rates of the various streams. The linear flow rates are preferably similar, although the relative flow rates are only limited by the occurrence of mixing between the sort stream and the media stream. Depending upon numerous factors such as the viscosities of the media and sort streams, the motility of the particles, and the presence or absence of particles or debris of different size than the particles desired to be sorted, the volume of the media stream may be less than, substantially the same as, or greater than the volume of the sort stream over any section of the sort channel.

The bulk of the description which follows is described in relation to sorting of sperm, although the same principles apply to other motile and non-motile particle sources.

In operation, a supply of sperm is introduced into sort stream inlet 2 and caused to flow toward motile particle-depleted sort stream outlet 9, initially through channel 7, then through sort channel 6, and next to outlet channel 9. A media supply stream compatible (i.e. not destructive) of the sperm to be sorted is introduced into media stream inlet 3 and caused to flow through channel 8 into sort channel 6, through channel 10, and into motile particle-enriched media outlet 5. At the confluence of channels 7 and 8, a non-mixing, and preferably laminar flow is created, such that the sort stream and media stream flow in parallel through the sort channel. Non-motile (or lesser-motile) particles tend to remain in the sort stream, while motile particles move about randomly and enter the media stream. As a result of this random movement, the sort stream becomes depleted of motile sperm, while the media stream becomes increasingly enriched.

The invention may further be described broadly with reference to FIGS. 2a, 2b, and 2c, which illustrate pictorially the separation of motile from non-motile sperm and other non-motile particles in the sort channel of the device of FIG. 1. In FIG. 2a, the sort channel 6 is shown, beginning at the point of confluence of the sort stream 11 and the media stream 12. The sort stream 11 contains motile 13 and non-motile sperm 14 as well as other non-motile particles, here designated as "round cells" 15. Note that the size of the media stream in plan, and hence its volume, is considerably greater than the sort stream. Since sperm (and similarly, other motile particles) assume an essentially random distribution in the total liquid within a short period, a larger media stream volume will necessarily contain a larger fraction of total motile sperm 13.

In FIG. 2b, the randomization of motile sperm between the two streams has begun, and continues until the desired degree of randomization has been achieved. This degree of randomization is preferably such that the concentration of motile sperm in the media phase per unit of volume is the same or greater than the concentration per unit volume in the sort stream. Note that the sort stream and media stream are maintained as separate streams, each preferably exhibiting laminar flow, and having a common boundary, or interface, 16. Greater concentration of motile particles in the media stream over the amount dictated by pure randomization may be achievable by employing a media stream in which the motile particles have increased mobility, i.e. by selecting a media stream less viscous than the sort stream, or by including additives which increase mobility of motile sperm relative to non-motile or poorly motile sperm.

In FIG. 2c, the motile sperm-enriched media stream is harvested by diverting it to flow into the motile particle-enriched channel 10, while the now motile particle-depleted sort stream continues through channel 9 into outlet 4.

The diverting juncture 17 which separates the motile particle-depleted sort stream from the motile particle-enriched stream may be of any geometry which avoids substantial mixing of the streams at this point. The juncture 17 may be positioned, for example, to provide for substantially the same outlet channel configuration (i.e. height, width) of the sort stream inlet, at this point. To minimize contamination of the media stream by non-motile sperm, the juncture 17 may also be configured such that a small portion of the media stream is also directed to the motile particle-depleted sort stream outlet 9. In this case, a modest loss of motile sperm will occur, however, the probability that non-motile sperm may enter the motile sperm-enriched media stream will be lessened as a result.

The nature of the sort stream is not critical. The sort stream may be a biologically derived stream such as semen, or may be washed, diluted, may be treated with additives, stains or fluorescing dyes, viscosity modifiers, may be buffered, etc., so long as the treatment does not impair the viability of the desired exit stream (motile particle-depleted or motile particle-enriched). If separation but not viability is the aim, for example with bacterial samples, the number of potential modifications of the sort stream are enlarged. The sort stream may also be a previously motile particle-depleted sort stream or motile particle-enriched media stream. For microrobotic devices, the sort stream liquid may be any which does not impair the functioning of the device, for example water, alcohols, ketones, glycols, esters, hydrocarbons, etc. With biological samples, water-based sort streams are ordinarily used.

The media stream may be selected with the same considerations in mind which are applied to selection or modification of the sort stream. In some cases, the sort stream may be water, but for biological systems, it is typical to employ streams which maintain or enhance biological activity, such as physiological saline, buffered saline, nutrient broths, and the like. In the case of human sperm, the preferred media is HEPES buffered human tubal fluid.

The nature of the media fluid and the sort fluid may be selected, if possible, to avoid interfacial mixing due to osmotic effects. This is the case, for example, when the base fluid (e.g. water) of both the sort and media streams have substantially the same amounts of soluble ingredients such as salts, acids, bases, buffers, dissolved organic material, and the like. The fluids may also be selected, when possible, to avoid interfacial mixing by diffusion. However, complete absence of any diffusion is an unlikely goal in this respect.

The relative fluid volumes may be selected with respect to the desired degree of incorporation of the motile particles within the media phase. For the highest degree of incorporation, the media volume should be large with respect to the sort fluid volume. However, proportionately smaller media volumes may also be used, particularly when sequential (serial) sorting is performed. Ratios of media fluid to sort fluid of from 1:1000 to 1000:1 are preferably used, more preferably 1:100 to 100:1, and most preferably within the range of 1:10 to 10:1. For typical applications, the ratio of media volume to sort fluid volume is within the range of 1:1 to 3:1. The media fluid volume is most preferably higher than the sort fluid volume.

The volumes referred to here are the volumes at a given cross-section of the sort channel. For example, a sort channel which is rectangular in shape having dimensions of 100 μm×200 μm will have a "transverse volume" of $2\times10^4$ μm$^2$. This "transverse volume," actually a cross-sectional area, can be converted into true volume by multiplying by channel length or an increment thereof. Thus, the same rectangular channel previously described and having a transverse volume of $2\times10^4$ μm$^2$ will have an actual volume over a 100 μm length of $2\times10^6$ μm$^3$.

The linear flow rates of the sort fluid and media fluid are preferably substantially the same, i.e. within a range of flow rates of 1.5:1 to 1:1.5. If the linear flow rate of the media fluid is greater than that of the sort fluid, correspondingly less transverse volume of media fluid can be used for the same degree of motile particle incorporation. Flow is preferably concurrent, although counterconcurrent flow is also possible provided that interfacial mixing is not exacerbated beyond that which facilitates the desired degree of depletion/enrichment of the sort and media fluids.

The interface between the sort and media fluids is preferably a substantially non-mixing interface. By "non-mixing" is meant an absence of mixing which occurs due to excessive turbulence between the two fluids. For example, it is most desired that parallel, concurrent, laminar flow take place such that a substantially "static" appearing interface is obtained, as opposed to an interface which exhibits waves, currents, eddys, and the like. Turbulent flow generally results in partial to full mixing of the streams, rendering depletion/enrichment of motile particles less efficient or even completely impossible. The theoretically best resolution of motile particles occurs when a static-appearing interface or "streamline" is created where interfacial mixing occurs only due to diffusional and osmotic effects. However, it would not depart from the spirit of the invention to allow some turbulence along the interface. The turbulence is excessive when the desired degree of resolution cannot be obtained, even with multiple stages of devices. The turbulence, expressed as a Reynolds number, should in any case be less than 2000, more preferably less than 100, yet more preferably less than 10, and most preferably 1 or less. High performance devices such as those illustrated by example herein, exhibit a Reynolds number of approximately 0.1.

The nature of the interface, i.e. its degree of turbulence, may be assessed by the degree of resolution. However, the turbulence may also be assessed in numerous additional ways. For example, in PDMS devices as described hereinafter, the optically transparent nature of the device allows the interface itself to be observed microscopically, for example by coloring one or both of the fluids and observing the interface by the change of color at the interface. By conventional optical techniques, the interface between media of differing refractive index are also easily observed. The degree of mixing of the sort and media streams may also be monitored by introducing a taggant, i.e. a radioactive soluble compound or non-motile particle, a visual or fluorescent dye, etc., into one stream but not the other. Appearance of the taggant in the outlet stream of the stream initially containing no taggant provides evidence of interfacial mixing, either of a turbulent kind, or by diffusion or osmosis. Some incorporation due to the latter two effects is expected, but is also expected to be quite minimal. An incorporation of 50% of the taggant into the non-tagged stream essentially constitutes complete mixing. Mixing of less than 20% of the taggant into the non-tagged stream, preferably less than 10%, more preferably less than 5%, and most preferably less than 1% is desired. So long as the Reynolds number is kept reasonably low, the degree of turbulence will be satisfactory. A flow which satisfies the above criteria is termed a "substantially non-turbulent flow" herein. It should be noted that concurrent flow streams exhibit much less turbulence, and hence interfacial mixing, than countercurrent flow streams.

Provided the fluid flow rate meets the non-turbulent requirements just described, the rate itself may vary widely. The walls of the sorting device also create the possibility for turbulence, since they are static with respect to the fluid flow. The effect of the walls will be most important when narrow channels are employed, and particularly at the walls which abut the narrower of the sort or media streams. Since the devices of interest are rather small and have rather small channels, linear flow rates of less than 10 cm/s, preferably less than 10 mm/s are preferred. Flow rates of between 0.1 mm/s to 10 mm/s are particularly preferred. The low end of linear flow rate is determined by the mixing of non-motile particles from the sort stream into the media stream by Brownian motion. For example, at a flow rate of zero, with identical base fluid compositions (e.g. buffered saline), distribution of non-motile particles into the media phase would eventually be complete over time such that their concentrations become identical. The higher the flow rate, the less Brownian redistribution of non-motile particles will occur. The upper limit of the flow rate is reached when the interfacial flow becomes turbulent, as evidenced by a high degree of mixing.

Determining the relative flow volumes, relative flow rates, and absolute flow rates of any given stream can be routinely accomplished by one skilled in the art by simple calculations and/or measurements of resolution, for example by varying the respective rates and volumes and determining the relative enrichment and depletion of particles between the sort and media streams.

The geometry of the devices can vary. Sort channel length, for example, is generally a function of the rapidity at which motile particles randomize themselves between the two phases, and the flow rates. For example, at a given flow rate, motile particles which have limited motility will require a longer sort channel, while at a given sort channel length, less motile particles will require a slower rate of flow. Interfacial surface area also effects the geometry of the device. For example, flat rectangular sort channels with one fluid located parallel to and abutting a channel face of greater dimension, and with the other fluid adjacent, will exhibit faster randomization and thus require less sort channel length than the same channel when the first fluid is located parallel to and abutting a channel face of lesser dimension. In the latter case, the interfacial area is much reduced as compared to the former.

While it is theoretically possible to construct devices of macroscopic size, even of greater than 10 cm in length, for most purposes, the sort channel will be quite short, in almost all cases less than 2-5 cm, and for most devices, in the range of 100 μm to 1 cm. For sperm sorting, for example, a sort channel length of 5000 μm (5 mm) has proven quite satisfactory. In staged devices, shorter sort channel lengths may be desirable.

The cross-sectional geometry of the sort channel is not critical. Square, rectangular, ellipsoidal, circular, trapezoidal, triangular or other cross-sections may be used. For ease of manufacturing, non-undercut channels such as square, rectangular, triangular, trapezoidal, and half-round or halfelliptical sections are preferred. These shapes are preferred, for example, when neat casting or solution casting methods of construction are employed. In the case of construction by stereolithography techniques ("SLA"), more complex shapes can easily be fabricated. Complex shapes with undercut channels can also be provided by casting techniques when the device is cast in successive layers which are then attached together, for example by bonding. However, the channel width must be such that both the media stream and sort stream can both incorporate particles. For human sperm sorting, for example, a substantially rectangular channel with a height of 50 µm and a width of 500 µm has proven satisfactory. For a point of reference, human sperm have a head of about 2.5 µm in diameter and about 5 µm long, and are about 60 µm in overall length.

The cross-sectional areas and hence size of the supply channels and outlet channels are generally smaller than those of the sort channel. The minimum size of the sort stream inlet channel is dictated by the size of the particles which are present in the sort stream. Preferably, the sort stream channel provides a free channel from 3 to 10 times the size of the particles expected to be contained therein. The same considerations apply to the size of the media stream outlet channel, but not necessarily to the media stream inlet channel. Preferably, the sort stream inlet and outlet channels will have comparable sizes, although in some instances, as described earlier, it may be desirable that the outlet channel is larger than the inlet, thus incorporating a portion of the media stream into the sort stream. For sperm sorting, a rectangular sort stream inlet channel of 50 µm height, 100 µm width, and 5000 µm length has proven satisfactory.

The length of the various inlet and outlet channels is not critical. It is preferred that at least the inlet channels have some substantial length, to encourage formation of a laminar flow stream prior to the confluence of the sort and media stream channels. In general, more viscous fluids will not require as long a channel length as less viscous fluids. In some cases, the inlet channels may be completely dispensed with, i.e. the sort stream inlet (or reservoir) and/or media stream inlet (or reservoir) may feed directly into the sort channel. For most purposes, however, and to facilitate construction of sorting devices, it is preferable that inlet channels be employed. For the sperm sorting device described later, for example, inlet channel lengths of about 3 mm have proven satisfactory.

The junction 18 (FIG. 1) of confluence of the sort and media streams is preferably configured to encourage a smooth joining of the fluid streams without excessive mixing. In general, therefore, the junction will be a relatively acute angle. The included angles between the sort stream inlet channel and the sort channel and between the media stream inlet channel and sort channel may be the same or different, i.e. the devices are not necessarily symmetrical. The same considerations apply to the junction 17 where the sort stream and media stream are separated, or "diverted" from each other. However, it is preferred that the sort stream inlet channel, sort channel, and sort stream outlet channel be substantially linear to provide as little disturbance of the non-motile particles in the sort stream as possible.

The material of construction of the sorting devices may be any suitable material, and the fabrication of the device may involve any fabrication process. For example, devices may be micromachined chemically by etching of glass, silica, silicon, metals, or by solution etching of polymers, etc. The devices may also be individually fabricated by known stereolithography techniques. The devices may be injection molded of moldable polymers, for example silicone rubber, thermoplastic polyurethane, polyethylene, polypropylene, polytetrafluoroethylene, polyvinyl chloride, polyvinylidene chloride, polyamide, polyester, and the like.

It is at present preferable to cast the sorting devices by supplying a negative "master" and casting a castable material over the master. Preferred castable materials are polymers, including epoxy resins, curable polyurethane elastomers, polymer solutions, i.e. solutions of acrylate polymers in methylene chloride or other solvents, and preferably, curable polyorganosiloxanes, most preferably for cost reasons, polyorganosiloxanes which predominately bear methyl groups, such as polydimethylsiloxanes ("PDMS"). Curable PDMS polymers are well known and available from many sources. Both addition curable and condensation-curable systems are available, as also are peroxide-cured systems. All these PDMS polymers have a small proportion of reactive groups which react to form crosslinks and/or cause chain extension during cure. Both one part (RTV-1) and two part (RTV-2) systems are available. Addition curable systems are preferred when biological particle viability is essential.

In many instances, transparent devices are desirable. Such devices may be made of glass or transparent polymers. PDMS polymers are well suited for transparent devices. A benefit of employing a polymer which is slightly elastomeric is the case of removal from the mold and the potential for providing undercut channels, which is generally not possible with hard, rigid materials. Methods of fabrication of microfluidic devices by casting of silicone polymers is well known. See, e.g. D. C. Duffy et al., "Rapid Prototyping of Microfluidic Systems in Poly(dimethylsiloxane)," ANALYTICAL CHEMISTRY 70, 4974-4984 (1998). See also, J. R. Anderson et al., ANALYTICAL CHEMISTRY 72, 3158-64 (2000); and M. A. Unger et al., SCIENCE 288, 113-16 (2000).

The nature of the channel and reservoir walls of the devices may be selected in view of the application of the device and the fluids contemplated for use therein. For example, the walls may be hydrophobic or hydrophilic, or some portions of the device may be hydrophobic while other portions are hydrophilic. In addition, the walls may be treated or derivatized to modify their surfaces with biologically compatible or bioactive coatings, or to provide chemical functionality. For sperm sorting, coating the channels with bovine serum albumin (BSA) has proven useful in improving liquid flow within the channels and to minimize non-specific adsorption of cells to channel walls.

Fluids may be supplied to the inlets or inlet channels of the device by any suitable method. Fluids may, for example, be supplied from syringes, from microtubing attached to or bonded to the inlet channels, etc. In preferred devices, the sort stream inlet and media stream inlet are in the form of "on-chip" reservoirs capable of holding and supplying the requisite amounts of liquids. These reservoirs may be filled by syringe, pipet, etc.

Fluid flow may be established by any suitable method. For example, external micropumps suitable for pumping small quantities of liquids are available. Micropumps may also be provided in the device itself, driven by thermal gradients, magnetic and/or electric fields, applied pressure, etc. All these devices are known to the skilled artisan. Integration of passively-driven pumping systems and microfluidic channels has been proposed by B. H. Weigl et al., PROCEEDINGS OF MICROTAS 2000, Enshede, Netherlands, pp. 299-302 (2000).

Preferably, however, fluid flow is established by a gravity flow pump, by capillary action, or by combinations of these methods. A simple gravity flow pump consists of a fluid reservoir either external or internal to the device, which contains fluid at a higher level (with respect to gravity) than the respective device outlet. Such gravity pumps have the deficiency that the hydrostatic head, and hence the flow rate, varies as the height of liquid in the reservoir drops. For many devices, a relatively constant and non-pulsing flow is desired.

To obtain constant flow, a gravity-driven pump as disclosed in published PCT application No. WO 03/008102 A1 (Jan. 18, 2002), herein incorporated by reference, may be used. In such devices, a horizontal reservoir is used in which the fluid moves horizontally, being prevented from collapsing vertically in the reservoir by surface tension and capillary forces between the liquid and reservoir walls. Since the height of liquid remains constant, there is no variation in the hydrostatic head.

Flow may also be induced by capillary action. In such a case, fluid in the respective outlet channel or reservoir will exhibit greater capillary forces with respect to its channel or reservoir walls as compared to the capillary forces in the associated inlet channel or reservoir. This difference in capillary force may be brought about by several methods. For example, the walls of the outlet and inlet channels or reservoirs may have differing hydrophobicity or hydrophilicity. Alternatively, and preferably, the cross-sectional area of the outlet channel or reservoir is made smaller, thus exhibiting greater capillary force.

Most preferably, integrated, on-board reservoirs which serve as constant flow rate gravity-driven pumps and which also exhibit a difference in capillary forces between inlet and outlet are used. Flow in such devices may begin as soon as the devices are filled with liquid or when blocking valves or plugs are opened, or may be initially assisted by a pressure differential between the inlet and outlet, for example by applying suction briefly to the outlet.

Multiple devices may be connected in many ways to effect complex separations, to provide enhanced yield, to provide increased resolution (sorting efficiency) or any combination of these. In addition, multiple sort and/or media streams may be employed. When multiple sort or media streams are used, the sort streams may be the same or different, as may be the media streams.

For enhanced efficiency, for example, the motile particle-depleted sort stream outlet of a device such as that depicted in FIG. 1 may be connected to the sort inlet of a second device, this second device also having a media supply. As a result of this sequential contact with two media streams, the sort stream will be further depleted of motile particles. The motile particle-enriched streams from both devices may be combined. Use of several sequential stages in this manner allows for virtually 100% recovery of motile particles. Preferably, when multiple devices are employed, they are fabricated on the same structure with integral connecting channels. One such device is shown schematically in FIG. 3.

In FIG. 3, the series configured two-stage motile particle sorter consists of a single sort fluid reservoir 20, connected to first sort channel 22 by sort stream channel 21. The first stage also consists of first media supply reservoir 23, media stream channel 24, motile particle-enriched first media channel 25, and motile particle-enriched first media reservoir 26. The motile particle-depleted sort outlet stream from the first stage flows through connecting passage 27 to serve as the sort stream inlet to the second stage sort channel 28. Second media reservoir 29 supplies media to the second stage sort channel through media inlet channel 30. Sort fluid further depleted of motile particles exits the device through channel 31 into motile particle-depleted sort stream reservoir 32, while a second stream of motile particle-enriched media fluid exits the sort channel through media outlet channel 33 and into reservoir 34. The two motile particle-enriched media reservoirs 26, 34 can be connected to a common exit channel or reservoir, optionally through valved passages, or may be emptied manually, e.g. using a syringe or pipet, and their contents combined, if desired.

Figure 5:
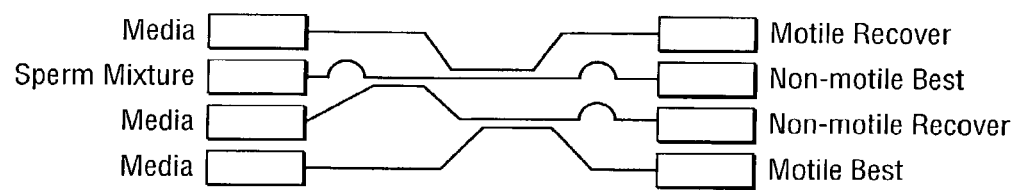
FIG. 5 illustrates in schematic form a further embodiment of a sorting device in accordance with the present invention.
Figure 6:
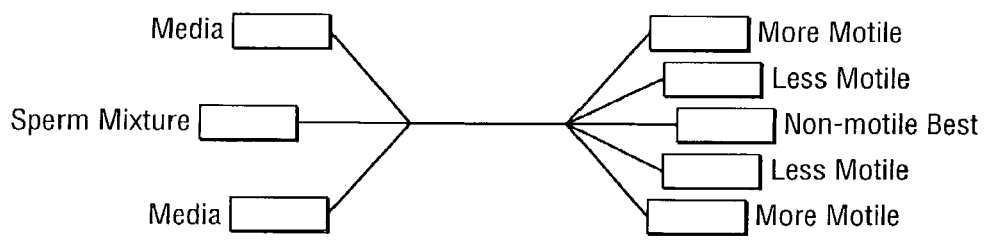
FIG. 6 illustrates in schematic form a further embodiment of a sorting device in accordance with the present invention.

Additional devices are shown in FIGS. 4, 5, and 6. In the device of FIG. 4, two media supply reservoirs 41 supply media fluid to the device 40, motile particle-enriched media being collected in the two media outlet reservoirs 42. A single sort fluid reservoir supplies fluid containing motile and non-motile particles from sort fluid reservoir 43, and the motile particle-depleted sort fluid is collected in sort fluid outlet reservoir 45 after passing through sort channel 44. In this case, a central sort stream 46 is flanked on each side by media streams 47.

FIGS. 5 and 6 are schematics of multiple stage devices which rely on alternative connections of various flow paths to improve one or more aspects of the sorting process. In both Figures, double lines represent sort channels. The device of FIG. 5 is capable of not only sorting motile from non-motile particles, but also into fractions of different motilities, and has three sort channels. The device of FIG. 6 splits the outlet of a single sort channel into fractions, the furthest away from the sort stream containing proportionately more of the particles with highest motility. As can be seen, the present devices can be configured simply or with great complexity. Devices may also operate in parallel, series parallel, or other modes. Parallel processing may be desired for sorting larger samples, or to measure sorting efficiency, etc., while comparing different media fluids. Such comparisons are more statistically accurate when measurements are made in a single device.

While much of the description herein refers to separation of motile from non-motile particles, the subject invention processes and devices are also suitable for separating motile particles of differing motility. The most motile particles will enter the media stream at a higher rate than particle's of lesser motility. The residence time in the sort channel is preferably selected such that the most motile particles will assume a random or near random distribution in the total fluid. In contrast to separation of motile from completely non-motile particles, however, where additional sort channel length can be tolerated, and distribution of non-motile particles into the media stream is due substantially only to Brownian motion and to turbulence and like effects, when motile and lesser motile particles are separated, the lesser motile particles will also assume a random distribution given sufficient time. The sort channel length must be adjusted downward such that this cannot occur. The media stream will be enriched with both motile and lesser motile particles, but will be correspondingly more greatly enriched by the particles of greater motility. Multiple sequential processing of a first media stream (serving as the sort stream to a further stage) will cause higher resolution between the differently motile particles. Second and further sorting of the sort streams and their subsequent treatment in like fashion will increase the yield.

Example 1

A microfluidic sperm sorting device was prepared from Dow Corning SYLGARD® 184 curable silicone resin, using the soft lithography technique described by D. C. Duffy et al., cited previously. The curable PDMS was cast onto a master having the desired reservoir and channel features as protuberances. The cast PDMS sorting devices were plasma oxidized to seal the open channel side of the casting to a glass cover slide. Channels and reservoirs were coated with 1% bovine serum albumin fraction V from Sigma, dissolved in phosphate buffered saline (PBS) from Invitrogen Corporation. The entire device was approximately 6 mm thick, exclusive of the cover slide, and somewhat larger than a U.S. penny coin. A perspective view of the device is shown in FIG. 7.

Figure 7:
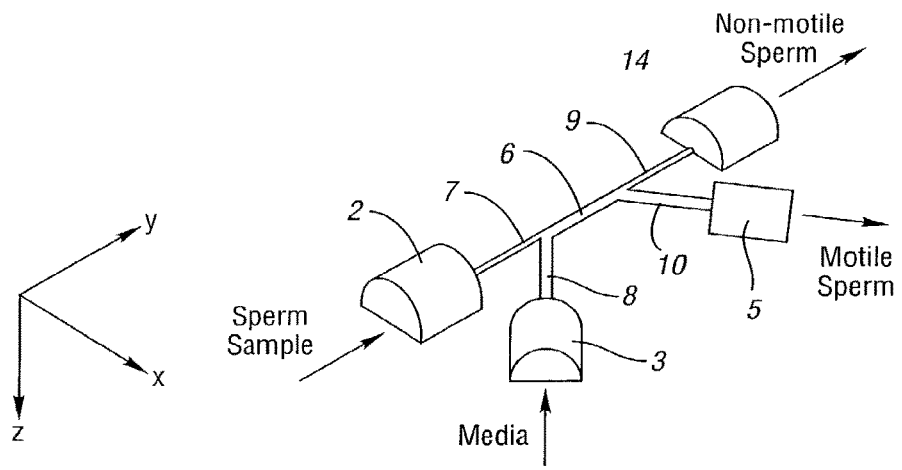
FIG. 7 illustrates a device similar to that of FIG. 1, in perspective.

In FIG. 7, the PDMS casting is transparent, and only the reservoirs and channels are depicted. The cover slide would be bonded to the bottom plane of the device. The numerals are the same as those of FIG. 1. The channels are rectangular in cross-section, with a channel height of 50 µm, while the reservoirs are roughly semi-circular. Both inlet reservoirs 2 and 3 are approximately 3 mm in height, while the outlet reservoirs are approximately 2 mm in height. The inlet and outlet channels 7, 8, 9, 10 are about 5000 µm long. The sperm inlet channel 7 and the motile depleted sperm outlet channel 9 have a width of 100 µm, while the media inlet channel 8 and outlet channel 10 have a width of about 300 µm. The sort channel 6 has a width of 500 µm and a length of 5000 µm.

Semen samples were obtained with institution Review Board approval from men undergoing infertility evaluation. Sorting tests were performed using washed semen samples. In the order listed, 60 µL of processing media was added to the media inlet reservoir, 50 µL of a washed semen sample to the sample inlet reservoir, and 2 µL of media to each of the outlet reservoirs. Sperm sorting yields were calculated taking these dilution factors into account. The numbers of motile sperm were determined by a Makler Counting Chamber (Sefi-Medical Instruments, Haifi, Israel). For visualization of membrane-compromised sperm, which generally corresponds to non-motile sperm, 3 µL of propidium iodide (Molecular Probes, www.probes.com, 60 mM dissolved in processing media) was added to sperm samples prior to sorting. A Texas Red filter set (577 nm excitation, 620 nm emission) was used to view red fluorescence from stained cells. An inverted microscope (NIKON TE 300, www.nikon-usa.com) with a CCD camera (Hamamatsu ORCA-100, www.hamamatsu.com) was used to capture images and record movies.

The sorting device uses a sorting system where non-motile sperm flow along their initial streamlines and exit one outlet whereas motile sperm can deviate from their initial streamlines and exit through a different outlet. This sorting mechanism is related to the "filtering" mechanism used in an "H-filter" where rapidly diffusing small molecules exit through a different outlet from larger molecules and particles that diffuse more slowly. The difference between the two devices is that the sorting device of the present invention takes advantage of active movement of cells whereas an H-filter takes advantage of passive diffusion of particles. This type of sorting is possible because in small channels, multiple laminar streams can flow parallel to each other with no turbulent mixing at the interface between the streams. Typical Reynolds Numbers for the flow of sperm sample and media inside the sorting device were on the order of 0.1. Non-motile human sperm, approximately 60 µm in length, and non-motile particles on the same order of magnitude in size diffuse slowly ($D=1.5\times10^{-13}$ m$^2$/sec; 690 sec to diffuse 10 µm) and remained within their initial streamlines. In contrast, motile human sperm swim at velocities greater than 20 µm/sec at 20° C. This rapid mobility allows motile sperm, but not the non-motile sperm, to distribute themselves randomly within the width of a 500 µm channel within seconds. The sorting device was designed specifically to give sperm a residence time of 20 seconds in the main separation channel. A bifurcation placed at the end of this separation channel allows efficient collection of only the motile sperm that deviated from its initial inlet stream.

The sorting device described integrates all functions necessary for sperm sorting, for example, inlet/outlet ports, fluid reservoirs, pumps, power source, sort channel, etc., onto a simple chip design that is practical to manufacture and use. A key design feature of this embodiment is the set of four horizontally-oriented fluid reservoirs that also function as sample inlet/outlet ports and a fluid pumping system. The orientation, geometry, and size of these reservoirs are designed to balance gravitational forces and surface tension forces, and provide a pumping system that generates a steady flow rate over extended periods of time regardless of the volume of fluid in the reservoirs. This contrasts with conventional gravity-driven pumping systems whose flow rates decrease over time as the volume of fluid in the inlet reservoir decreases. The diameters of the reservoirs were selected to be small enough that surface tension prevents liquid from spilling out of the horizontally-oriented reservoirs, but large enough to hold sufficient amounts of sample (tens to hundreds of microliters) and allow convenient sample introduction and recovery. This balance of forces allows the reservoirs to be arranged horizontally without the liquid inside spilling out. The horizontal reservoir arrangement, in turn, holds the height difference between the fluid in the inlet and outlet reservoirs the same (1.0 mm height difference between inlet and outlet reservoir ceilings) regardless of the volume of fluid present in the reservoirs and maintains a constant hydraulic pressure even as the amount of fluid in the reservoirs changes.

The passively-driven pumping system described here is unique in that it uses horizontally-oriented reservoirs to overcome the problem of traditional gravity-driven pumping, where the pressure decreases as the amount of liquid in the reservoir decreases. Furthermore, the structure of the pump is greatly simplified compared to other mechanical or non-mechanical pumping systems allowing easy manufacture and integration of the pump into a small, integrated device. Finally, the use of gravity and surface tension as the driving-force contributes to the overall small size of the sorting device by eliminating the need for power supplies such as batteries. Taking gravity, surface tension, and channel resistance into consideration, the sorting device was designed to give a steady flow rate of sperm with a residence time of approximately 20 seconds inside the main sort channel. More specifically, the device is designed so that the flow resistance of the fluid reservoirs is more than 10 times less than that of the microfluidic channels, and therefore negligible. Thus, the resistance of the channels, calculated to be $2.8\times10^{12}$ kg/(sec/m$^4$), approximates the total resistance of the system. Since a bulk flow rate of 0.008 µL/sec is required to achieve the desired residence time of 20 seconds and the total resistance is $2.8\times10^{12}$ kg/(sec/m$^4$), the net pressure drop required to drive the fluid is 23 N/m$^2$. To achieve this desired pressure drop, we designed the dimensions of the reservoirs such that capillary forces (3.0 mm diameter inlet reservoir vs. 2.0 mm diameter outlet reservoir) would be 13 N/m$^2$ and the pressure drop across the microfluidic channel of the sorting device due to hydrostatic forces (1.0 mm height difference) would be 9.8 N/m$^2$. For calculation of the capillary force, the contact angle was assumed to be 0° (the contact angle of water on BSA coated PDMS is very small), the surface tension of the washed semen sample assumed to be approximately 0.040 N/m (less than that of water due to "impurities" such as proteins), and the viscosity of the washed semen sample to be similar to that of water. The observed bulk flow rate of 0.008 µL/sec for a dilute particle suspension in 1% BSA solution was approximately equal to that of the calculated flow rate. Actual sperm samples sometimes had lower flow rates due to larger apparent viscosity. Smaller flow rates for the sperm sample stream would result in slightly lower yields but does not affect the purity of the sperm recovered at the sorted sperm outlet.

Figure 8:
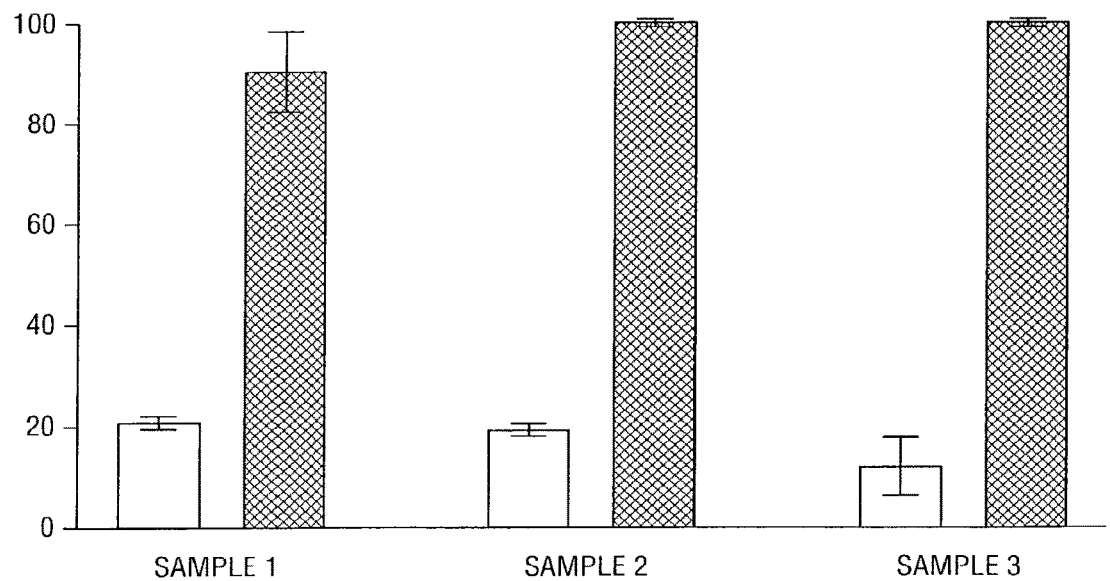
FIG. 8 illustrates sorting efficiency of a device similar to that of FIG. 1 in sorting sperm.

Sperm sorting efficiencies of the sorting device were evaluated by three methods: (i) tracking the movement of motile sperm in the channel by phase contrast microscopy, (ii) tracking movement of propidium iodide (PI) stained cells in the channel by fluorescence microscopy, (iii) using a Makler Counting Chamber, a grid-based sperm counting device, to determine numbers of motile sperm and non-motile sperm in the inlet and outlet reservoirs (FIG. 8). The sperm tracking experiments shows the process of how motile sperm can swim out of its initial streamline. PI stains membrane compromised cells such as dead cells, and thus allows the non-motile sperm to be highlighted and visualized with red fluorescence while the motile sperm remain unstained. The bar graphs in FIG. 8 compare percentage of sperm that are motile before and after sorting. The unshaded bars represent the initial sperm sample, while the solid bars represent the motile particle-enriched media stream. The purity of motile sperm after sorting was nearly 100% regardless of motile sperm purity before sorting. The yields (39%, 42%, 43%), defined as the ratio of the number of motile sperm in the motile sperm outlet reservoir to the total number of motile sperm in the sperm sample inlet reservoir, were comparable to or greater than the recovery rates (0.8% to 50%) of sperm processed using conventional sorting methods such as direct swim-up, swim-up from a pellet of centrifuged sperm, or density gradient separation. It was also observed that sperm morphology, another important trait that correlates with successful pregnancies, also improved after sorting with the device (Strict Sperm Morphology: 9.5±1.1% normal before sorting to 22.4±3.3% normal after sorting). Kruger Strict sperm morphology is a set of criteria or standards whereby sperm must fit within specific measurements (head width and length, tail length, acrosome making up a certain percentage of the sperm head) and lack abnormalities (e.g. pin head, round head, crimped tail).

As can be seen from the above, the motile particle sorting devices are small, easily manufactured, simple in operation, and highly efficient. In the claims which follow, the terms "a" and "an" mean "one or more than one" unless indicated otherwise.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for sorting motile sperm from lesser motile and/or non-motile sperm, comprising:

a) providing a sort fluid comprising motile sperm and at least one of lesser motile sperm or non-motile sperm;
b) providing a media fluid to be enriched with motile sperm;
c) contacting a stream of said sort fluid and a stream of said media fluid within a sort channel of a sorting device, wherein said sorting device comprises i) a sort channel having first and second ends, wherein said sort channel has a length of less than 5 cm; ii) a sort fluid reservoir in fluid communication with said first end of said sort channel; iii) a media fluid reservoir in fluid communication with said first end of said sort channel; iv) a motile particle-depleted sort fluid outlet in fluid communication with said second end of said sort channel; and v) a motile particle enriched media fluid outlet in fluid communication with said second end of said sort channel; said sort fluid stream and said media fluid stream having there between a non-turbulent interface within said sort channel, wherein said media fluid reservoir acts as a gravity flow pump to transport said media fluid through said sort channel, whereby motile sperm leave the sort fluid stream and enter the media fluid stream by active movement, forming a motile particle-depleted sort fluid stream and a motile particle-enriched media fluid stream, wherein said sperm move perpendicular to gravity and perpendicular to the direction of flow of said media fluid in said sort channel during said step of whereby said motile sperm leave the sort fluid stream and enter the media fluid stream, and d) separating a motile sperm-depleted sort fluid outlet stream from a motile sperm-enriched media fluid outlet stream to isolate motile sperm, wherein said motile sperm are alive.

2. The process of claim 1, wherein said sort fluid is provided in a sort fluid reservoir and said media fluid is provided in a media fluid reservoir.

3. The process of claim 1, wherein said media fluid and said sort fluid flow in the same direction and at substantially the same flow rate.

4. The process of claim 1, wherein said sort fluid stream and said media fluid stream exhibit laminar flow within said sort channel.

5. The process of claim 1, wherein the transverse volume of said media fluid stream is greater than the transverse volume of said sort fluid stream in said sort channel.

6. The process of claim 1, wherein said motile sperm depleted sort fluid outlet stream comprises a sort fluid inlet stream to a second device having a sort channel, and steps a) through d) are repeated, whereby further motile sperm enter a media stream of said second device to further deplete said sort fluid of motile sperm.

7. The process of claim 1, wherein the purity of motile sperm after sorting is between 90% and 100%, wherein said percent is based on the number of motile sperm in said motile particle-enriched media outlet stream compared to total sperm in said motile particle-enriched media outlet stream and said motile particle-depleted sort fluid stream.

* * * * *